US010640454B2

(12) United States Patent
Bellandi et al.

(10) Patent No.: US 10,640,454 B2
(45) Date of Patent: May 5, 2020

(54) PROCESSES FOR PREPARATION OF 4-AMINOINDANE COMPOUNDS AND RELATED AMINOINDANE AMIDES

(71) Applicant: STICHTING I-F PRODUCT COLLABORATION, Amsterdam (NL)

(72) Inventors: Paolo Bellandi, Carcare (IT); Giampaolo Zanardi, Novara (IT); Ravindra Vitthal Datar, Bangalore (IN); Chockalingam Devarajan, Tamil Nadu (IN); Swamynathan Murali, Bangalore (IN); Narayana Swamy, Bangalore (IN)

(73) Assignee: STICHTING I-F PRODUCT COLLABORATION, Amsterdam (NL)

( * ) Notice: Subject to any disclaimer, the term of this patent is extended or adjusted under 35 U.S.C. 154(b) by 0 days.

(21) Appl. No.: 16/091,764

(22) PCT Filed: Apr. 15, 2016

(86) PCT No.: PCT/IB2016/052169
§ 371 (c)(1),
(2) Date: Oct. 5, 2018

(87) PCT Pub. No.: WO2017/178868
PCT Pub. Date: Oct. 19, 2017

(65) Prior Publication Data
US 2019/0119195 A1 Apr. 25, 2019

(51) Int. Cl.
C07C 209/62 (2006.01)
C07D 211/60 (2006.01)
C07C 209/70 (2006.01)
C07C 231/02 (2006.01)
C07C 231/08 (2006.01)
C07C 231/14 (2006.01)

(52) U.S. Cl.
CPC .......... C07C 209/62 (2013.01); C07C 209/70 (2013.01); C07C 231/02 (2013.01); C07C 231/08 (2013.01); C07C 231/14 (2013.01); C07D 211/60 (2013.01); C07C 2602/08 (2017.05)

(58) Field of Classification Search
None
See application file for complete search history.

(56) References Cited

U.S. PATENT DOCUMENTS

| | | | |
|---|---|---|---|
| 4,742,074 A * | 5/1988 | Nishida | A01N 43/56 514/406 |
| 5,093,347 A | 3/1992 | Graneto et al. | |
| 2015/0164076 A1 | 6/2015 | Pellacini et al. | |
| 2015/0344431 A1* | 12/2015 | Matsunaga | C07D 215/04 546/181 |

FOREIGN PATENT DOCUMENTS

| | | |
|---|---|---|
| EP | 0 199 822 A1 | 11/1986 |
| EP | 0 256 503 A2 | 2/1988 |
| EP | 0 276 177 A1 | 7/1988 |
| EP | 0 280 275 A2 | 8/1988 |
| EP | 0 569 912 A1 | 11/1993 |
| EP | 0 654 464 A1 | 5/1995 |
| JO | 2015519384 A | 7/2015 |
| JP | S6296471 A | 5/1987 |
| JP | H01313402 A | 12/1989 |
| JP | H02157266 A | 6/1990 |
| JP | H02249966 A | 10/1990 |
| JP | H07215921 A | 8/1995 |
| JP | H1070479 A | 3/1998 |
| JP | H1117864 A | 1/1999 |
| JP | 3077381 B2 | 8/2000 |
| WO | 1986002641 A1 | 5/1986 |
| WO | 2001/053259 A1 | 7/2001 |
| WO | 2004/018438 A2 | 3/2004 |
| WO | 2004/039789 A1 | 5/2004 |
| WO | 2004/072023 A2 | 8/2004 |
| WO | 2004/103975 A1 | 12/2004 |
| WO | 2005/075452 A1 | 8/2005 |
| WO | 2010109301 A1 | 9/2010 |
| WO | 2012/084812 A1 | 6/2012 |
| WO | 2013/186325 A1 | 12/2013 |

(Continued)

OTHER PUBLICATIONS

Cliffe ("The Acid-catalysed Rearrangement of Tetrahydroquinoline Derivatives" J. Chem. Soc. (C), 1966, p. 514-517) (Year: 1966).*
Chen ("Effect of Tetrahydroquinoline Dyes Structure on the Performance of Organic Dye-Sensitized Solar Cells" Chem Mater, 19, p. 4007-4015, 2007, including SI p. S1-S30) (Year: 2007).*
Vaughan, Organic Syntheses, Working with Hazardous Chemicals, paragraphs added in Sep. 2014, 2,4-Dimethylquinoline [Quinoline, 2,4-dimethyl-], Organic Syntheses, Coll. vol. 3, p. 329 (1955); vol. 28, p. 49 (1948).

(Continued)

Primary Examiner — Amy C Bonaparte
(74) Attorney, Agent, or Firm — MH2 Technology Law Group, LLP

(57) ABSTRACT

A process for preparation of 4-aminoindane derivatives of a first formula, salts and enantiomers thereof comprising the steps of: a) hydrogenating a 1,2-dihydroquinoline of a second formula to give a corresponding tetrahydroquinoline of a third formula; b) acylating the tetrahydroquinoline of the third formula with a carboxylic acid derivative of a fourth formula to obtain a corresponding acyl derivative compound of a fifth formula; c) rearranging the acyl derivative compound of the fifth formula under acidic conditions so as to give an acyl indane compound of a sixth formula; and d) hydrolysing the acyl group of the acyl indane compound of the sixth formula so as to obtain the 4-aminoindane derivatives of the first formula.

20 Claims, No Drawings

(56) References Cited

FOREIGN PATENT DOCUMENTS

WO     WO 2014103811      *   7/2014
WO     WO-2014103811 A1 *   7/2014  ........... C07C 209/84

OTHER PUBLICATIONS

International Search Report and Written Opinion dated Jan. 5, 2017, in corresponding PCT Application No. PCT/IB2016/052169, 13 pages.
Japanese Office Action in corresponding Japanese Application No. 2018-553223 dated Jan. 14, 2020, 4 pages.

* cited by examiner

PROCESSES FOR PREPARATION OF 4-AMINOINDANE COMPOUNDS AND RELATED AMINOINDANE AMIDES

CROSS-REFERENCE TO RELATED APPLICATION(S)

This application is a national stage entry from International Application No. PCT/IB2016/052169, filed on Apr. 15, 2016, in the Receiving Office ("RO/IB") of the International Bureau of the World Intellectual Property Organization ("WIPO"), published as International Publication No. WO 2017/178868 A1 on Oct. 19, 2017, the entire contents of all of which are incorporated herein by reference.

The present invention relates to a process for the preparation of 4-aminoindane derivatives of Formula (I)

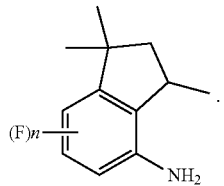
(I)

The present invention also relates to a process for the preparation of aminoindane amides of Formula (II), having fungicidal activity, starting from a 4-aminoindane derivative intermediate of Formula (I) obtained through the above-mentioned process.

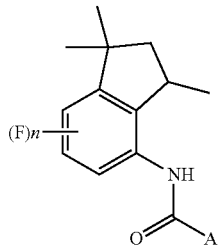
(II)

BACKGROUND OF THE INVENTION

Aminoindane amides as well as the processes for the preparation thereof have been widely reported in the prior art, such as in JP1070479, JP1117864, JP1313402, JP2157266, JP2249966, JP3077381, JP62096471, EP199822, EP256503, EP276177, EP280275, EP569912, U.S. Pat. No. 5,093,347, WO01/53259, WO2004/018438, WO2004/039789, WO2004/072023, WO2004/103975, WO2005/075452, WO2012/084812 and WO2013/186325.

In particular, WO2013/186325 discloses that the compound 3-difluoromethyl-N-(7-fluoro-1,1,3-trimethyl-4-indanyl)-1-methyl-4-pyrazolecarboxamide can be prepared in four steps starting from 4-fluoroaniline and acetone. These two compounds are first condensed together to form a substituted dihydroquinoline, which is then hydrogenated to afford the corresponding tetrahydroquinoline. The tetrahydroquinoline is then reacted with a pyrazole carboxylic acid derivative and the resulting compound is subjected to acid rearrangement to provide the corresponding aminoindane amide derivative. The 4-step preparation is reported below in Scheme 1.

Scheme 1

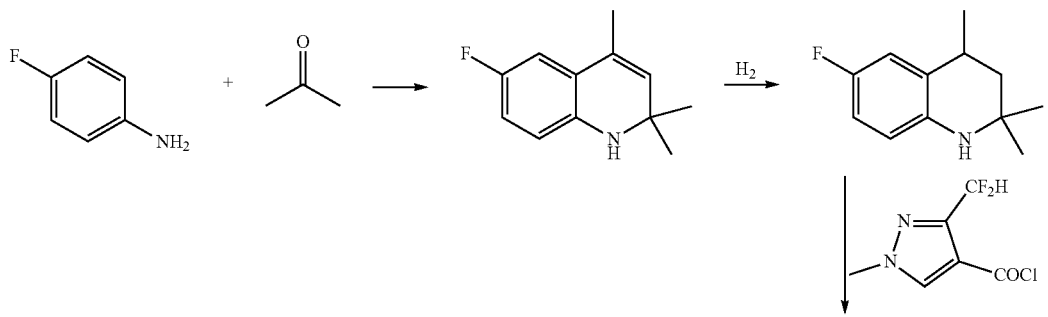

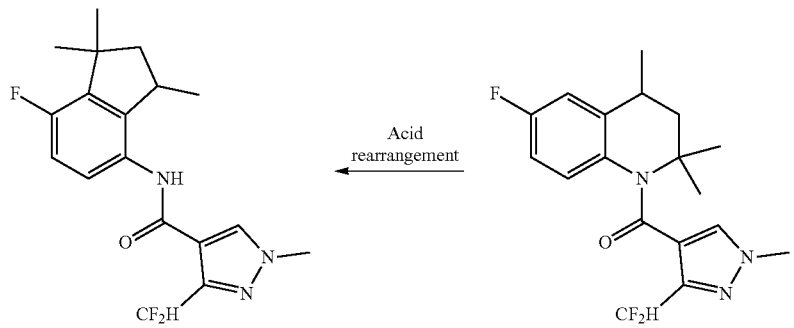

However, said process is not satisfactory since from a chemical point of view, the secondary amine in the tetrahydroquinoline ring is quite difficult to acylate; therefore, forcing reaction conditions such as addition of an excess of a base and the use of a chlorinated organic solvent are needed so as to obtain the corresponding acyl tetrahydroquinoline. Moreover, the overall yields of this process are relatively low and lead to a significant loss of the pyrazole acid chloride derivative, which is an expensive material.

It is also known that 4-aminoindane derivatives can be used as key intermediates for synthesizing aminoindane amide derivative. An example of such a synthesis can be found in EP199822, which discloses that aminoindane amide derivatives can be obtained through a condensation reaction between a pyrazole carboxylic acid halide and a 4-aminoindane derivative, as reported below in Scheme 2.

Scheme 2

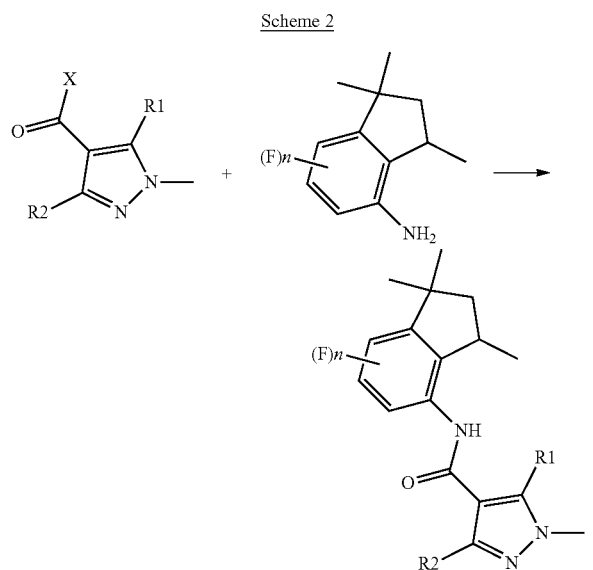

However, in EP199822 there is no indication about the synthetic pathway for preparing the 4-aminoindane derivative.

Few prior art documents actually describe a process for the preparation of such 4-aminoindane derivatives.

For example, EP654464 discloses that 4-aminoindane derivatives in diastereoisomerically-enriched form can be obtained in four steps, as reported in Scheme 3: i) condensation between a dihydroquinoline and a carboxylic acid derivative bearing both a chiral center (indicated with * in the scheme below) and a terminal leaving group LG; ii) catalytic hydrogenation to provide the corresponding tetrahydroquinoline; iii) addition of a strong acid to obtain the corresponding 4-aminoindane derivative; and iv) hydrolysis of the amide bond.

Scheme 3

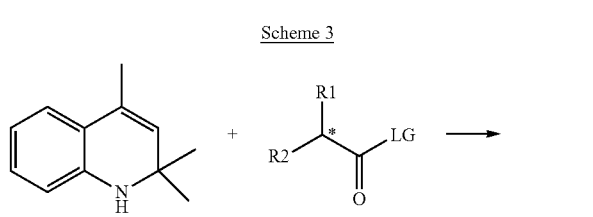

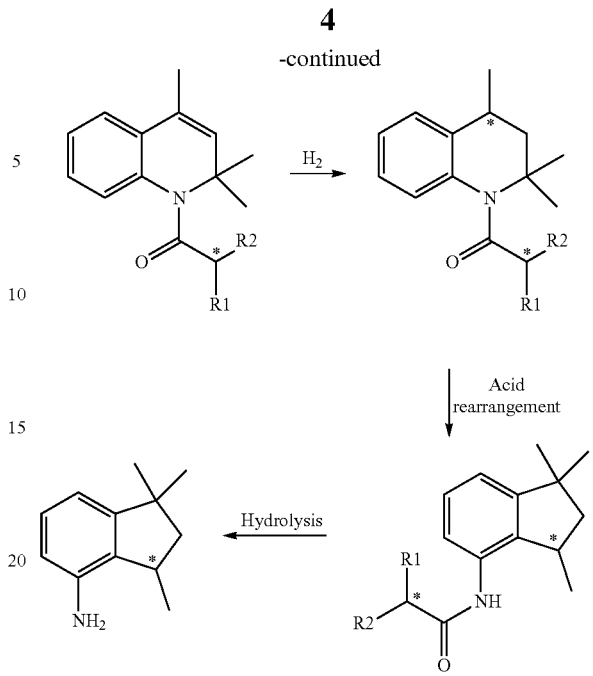

However, the above-mentioned process for the preparation of the 4-aminoindane derivatives is not satisfactory from an industrial point of view, since it requires to use a different solvent for each step (i.e. tetrahydrofuran, methanol and sulphuric acid+water+acetic acid in Example 1, Route N. 1, page 9). Therefore, additional operations are to be performed at the end of any single reaction step in order to avoid for instance, contamination of the subsequent reaction mixture by a remaining chemical or solvent.

Moreover, the acyl dihydroquinoline and the corresponding tetrahydroquinoline are scarcely soluble in apolar solvents, such as aliphatic hydrocarbons. Consequently, in order to completely convert the acyl dihydroquinoline into the corresponding tetrahydroquinoline, higher reaction temperatures or dilution of the reaction mixture are required.

It is therefore desirable to provide an easier process for preparing aminoindane derivatives, in particular aminoindane amides on a large scale, which would reduce costs and production times.

DESCRIPTION OF THE INVENTION

It has now been surprisingly found that, by inverting the hydrogenation and condensation steps of the process disclosed in EP654464, it is possible to prepare 4-aminoindanes derivatives and the corresponding aminoindane amides in a simpler and more cost-effective way.

A first object of the present invention is therefore a process for the preparation of 4-aminoindane derivatives of Formula (I), salts and enantiomers thereof (I)

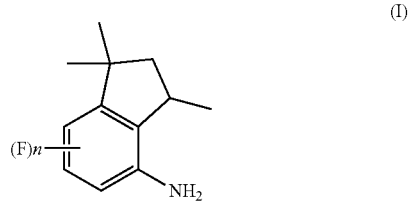

comprising the following steps:
  a) hydrogenating a 1,2-dihydroquinoline of Formula (IV)

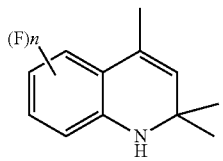

(IV)

to give a corresponding tetrahydroquinoline of Formula (V)

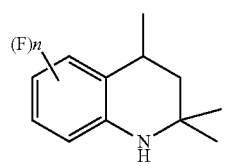

(V)

b) acylating the tetrahydroquinoline of Formula (V) with a carboxylic acid derivative of Formula RC(O)LG to afford an acyl derivative compound of Formula (VI)

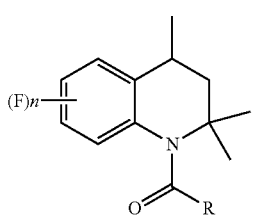

(VI)

c) rearranging the acyl derivative compound of Formula (VI) under acidic conditions to give an acyl indane compound of Formula (VII)

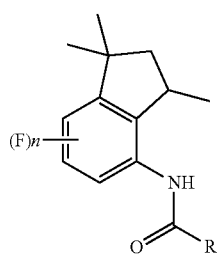

(VII)

d) hydrolysing the acyl group of the acyl indane compound of Formula (VII) to provide the desired 4-aminoindane of Formula (I),
wherein in said formulae:
  n is an integer selected within the range from 0 to 3;
  R is a $C_1$-$C_6$ alkyl group, a $C_6$-$C_{10}$ aryl group, these groups being optionally substituted with one or more of: $C_1$-$C_6$ alkyl group, halogen atom;
  LG is a leaving group selected from: (i) a hydroxy group; (ii) a halogen atom; (iii) a $C_1$-$C_6$ alkylsulfonyloxy group; (iv) a $C_6$-$C_{10}$ arylsulfonyloxy group; (v) a $R_aCOO$ group wherein $R_a$ is a $C_1$-$C_6$ alkyl group, the groups (iii)-(v) being optionally substituted with one or more halogen atoms.

The process object of the present invention comprises at least the four steps indicated above, which are carried out in the indicated order.

As evidenced by the experimental data included in the present description, the Applicant has surprisingly found that by inverting the steps of hydrogenation and condensation (acylation) of the process disclosed in EP654464 it becomes possible to use only one type of organic solvent (e.g. an aliphatic hydrocarbon, such as heptane) in the whole production process of the 4-amnoindane derivatives of Formula (I), thus simplifying the process and reducing its costs and production times.

Moreover, the preparation process according to the present invention can be advantageously carried out by performing the steps (a) to (c) without being necessary to isolate and/or purify the intermediate products of the Formulae (VI) and (VII) at the end of their respective formation steps.

The present invention thus provides a more cost-effective route for the preparation of 4-aminoindane derivatives of Formula (I) as well as of other compounds of industrial and commercial interest which are typically prepared starting from these 4-aminoindane derivatives, such as the aminoindane amides of Formula (II) which can be used as fungicides. According to the presently claimed process, in the step (a) a 1,2-dihydroquinoline of Formula (IV) is first subjected to catalytic hydrogenation, as reported below in Scheme 4.

Scheme 4

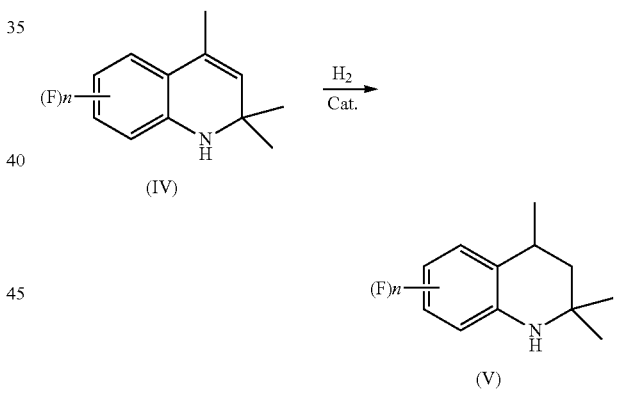

The compound of Formula (IV) is either commercially available or can be prepared, for instance, as described in Organic Synthesis, Vol. III, pag. 329. According to a preferred aspect of the present invention, an aniline derivative of Formula (III) is condensed with acetone in presence of an acidic catalyst to afford the corresponding dihydroquinoline of Formula (IV), as reported below in Scheme 5.

Scheme 5

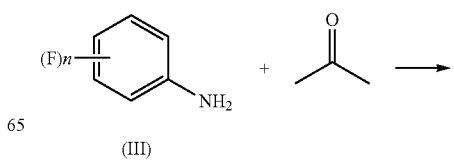

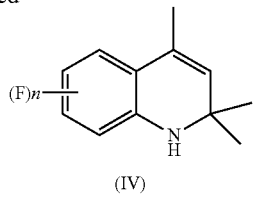

(IV)

The aniline derivative of Formula (III) is reacted with acetone, in a quantity comprised between 1 and 15 molar equivalents, preferably between 3 and 10 molar equivalents, more preferably between 4 and 7 molar equivalents, with respect to the starting aniline of Formula (III).

Preferably, the acetone is added to said aniline derivative of Formula (III) during a time comprised between 1 and 15 hours, more preferably between 2 and 12 hours, even more preferably between 5 and 10 hours. To the mixture thus formed, an acidic catalyst is added, preferably an acidic catalyst selected from an organic acid, an inorganic acid or a mixture thereof. Non-limiting examples of suitable acidic catalysts according to the present invention are: methanesulfonic acid, paratoluenesulfonic acid, acetic acid, tetrafluoboric acid, hydrochloric acid, hydrobromic acid, sulfuric acid or mixtures thereof.

Most preferred acidic catalysts are selected from tetrafluoboric acid and paratoluenesulfonic acid.

During the addition of the acetone to the aniline derivative of Formula (III), the reaction mixture is kept at a temperature comprised between 80° C. and 200° C., preferably between 100° C. and 180° C., more preferably between 125° C. and 145° C.

When the reaction is complete, the dihydroquinoline derivative of Formula (IV) thus obtained can be isolated and purified according to methods well known to those skilled in the art. For example, the reaction mixture can be treated with a base, such as an inorganic base, to remove free acidity and extracted by mixing it with an organic solvent slightly-miscible or immiscible with water. The desired 1,2-dihydroquinoline product can be recovered for instance by fractional distillation.

According to a preferred aspect of the present invention, the residual aniline derivative of Formula (III) can also be recovered by fractional distillation and advantageously reused in the subsequent production batch.

According to the present invention, in the step (a) the compound of Formula (IV) is dissolved in an organic solvent, preferably a polar organic solvent, and a metal catalyst is added to the reaction mixture.

Said metal catalyst is preferably an heterogeneous catalyst, more preferably selected from palladium on charcoal, palladium hydroxide on charcoal, Raney nickel and platinum oxide; even more preferably the metal catalyst is palladium on charcoal.

According to the present invention, the catalyst loading is comprised between 0.05 and 0.7%, preferably comprised between 0.1 and 0.6%, more preferably the loading is of about 0.5%, with respect to the molar amount of dihydroquinoline of Formula (IV).

Non-limiting examples of solvents that can be used in the hydrogenation reaction are: aliphatic or cycloaliphatic hydrocarbons (e.g. petroleum ether, hexane, cyclohexane, heptane), chlorinated hydrocarbons (e.g. methylene chloride, chloroform, carbon tetrachloride, dichloroethane), aromatic hydrocarbons (e.g. benzene, toluene, xylene, chlorobenzene), alcohols and glycols (e.g. methanol, ethanol, isopropanol, ethylene glycol), esters (e.g. ethyl acetate, butyl acetate) or mixtures thereof.

Among these, the preferred solvents are: aliphatic hydrocarbons, such as hexane and heptanes; chlorinated hydrocarbons, such as methylene chloride and dichloroethane; alcohols, such as methanol, ethanol and isopropanol; toluene; ethyl acetate.

Heptane, dichloroethane, methanol and toluene are particularly preferred.

Within the meaning of the present invention, the term "heptane" refers either to n-heptane or to a mixture of isomers.

As it is well known to the skilled person, the hydrogenation reaction of step a) can be carried out at a pressure greater than 1 bar or at atmospheric pressure.

Preferably, the step a) of the present invention is carried out at atmospheric pressure.

When the step a) is carried out at atmospheric pressure, the catalyst loading is preferably of about 0.5% and the reaction mixture is left to react for a time preferably comprised between 1 and 5 hours at room temperature.

When the step a) is carried out under a hydrogen overpressure, said overpressure is preferably comprised between 5 to 9 bar.

When the step a) is carried out under a hydrogen overpressure, the catalyst loading is preferably comprised between 0.1 and 0.6% and the reaction mixture is left to react for a time preferably comprised between 10 and 18 hours at a temperature preferably comprised between 35 and 50° C.

At the end of step (a), the catalyst is recovered and preferably reused for subsequent production batches.

The tetrahydroquinoline of Formula (V) obtained in the hydrogenation step a) is isolated from the reaction mixture by methods well known to those skilled in the art, for example by solvent concentration.

Preferably, the isolated compound of Formula (V) is not purified and it is used as such in the subsequent step of the process.

Step b) of acylation is performed by adding a carboxylic acid derivative of Formula RC(O)LG to the tetrahydroquinoline of Formula (V), as reported below in Scheme 6.

Scheme 6

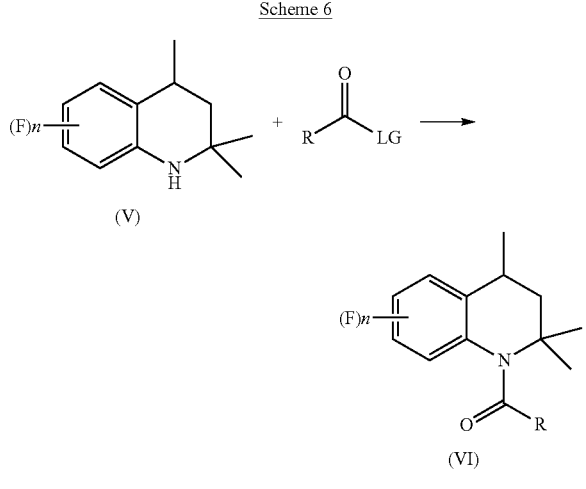

in which:
R is a $C_1$-$C_6$ alkyl group, a $C_6$-$C_{10}$ aryl group, these groups being optionally substituted by one or more of: $C_1$-$C_6$ alkyl groups, halogen atoms;
LG is a leaving group selected from: (i) a hydroxyl group; (ii) a halogen atom; (iii) a $C_1$-$C_6$ alkylsulfonyloxy group; (iv) a $C_6$-$C_{10}$ arylsulfonyloxy group; (v) a $R_a$COO group wherein $R_a$ is $C_1$-$C_6$ alkyl group, the groups (iii)-(v) being optionally substituted with one or more halogen atoms.

Preferably, the carboxylic acid derivative is added in an amount comprised between 5 and 30%, more preferably between 10 and 25%, with respect to the molar quantity of the starting tetrahydroquinoline of Formula (V).

According to a more preferred aspect, the carboxylic acid derivative is selected from acetyl chloride and acetic anhydride, even more preferably the carboxylic acid derivative is acetic anhydride.

The acylation reaction can be carried out in an organic solvent or in the absence of a solvent. According to the present invention, said reaction is preferably carried out in the absence of any added solvent.

In the step c), the reaction mixture is maintained at a temperature comprised between 80° C. and 200° C., preferably comprised between 100° C. and 150° C., more preferably of about 130° C.

If the acetic anhydride is used, once the conversion is complete, some water is preferably added to cause decomposition of the residual acetic anhydride to acetic acid.

In order to completely remove the residual acetic acid, a solvent immiscible with water can be added to the reaction mixture, preferably an aliphatic hydrocarbon such as hexane or heptane.

According to a preferred aspect of the present invention, the acetic acid is removed from the reaction mixture by vacuum distillation/azeotropic distillation with heptane.

The acyl tetrahydroquinoline of Formula (VI) obtained at the end of the acylation step can be purified according to methods well known to the skilled person, for example, by precipitation, crystallization and the like.

Preferably, said acyl tetrahydroquinoline of Formula (VI) is subjected to crystallization with an organic solvent thus forming a slurry with that solvent. Advantageously, according to the present invention, the solvent used for the crystallization is of the same type as the solvent used for removing the residual acetic acid.

The acyl tetrahydroquinoline of Formula (VI) contained in said slurry is preferably not isolated. The slurry can be used as such in the next step.

Subsequently, the acyl tetrahydroquinoline of Formula (VI) is subjected to rearrangement in acidic environment, as reported below in Scheme 7.

The acidic pH condition which allows the rearrangement of the tetrahydroquinoline of Formula (VI) to give the corresponding indane derivative of Formula (VII) can be obtained by addition of an organic or inorganic acid to the compound of Formula (VI).

Preferably, an inorganic acid is added, more preferably an inorganic acid selected from orthophosphoric acid and sulfuric acid, even more preferably the inorganic acid is sulfuric acid.

Said inorganic or organic acid is added in an amount comprised between 3 and 10 molar equivalents, preferably between 4 and 9 molar equivalents, more preferably between 6 and 7 molar equivalents, with respect to the tetrahydroquinoline of Formula (VI).

According to a more preferred aspect of the present invention, the concentration of the acid is comprised between 80% and 98%, even more preferably between 90% and 97%.

Since the acid dissolution is exothermic, the temperature of the reaction mixture is to be controlled.

Therefore, according to the presently claimed process, the reaction mixture is preferably kept at a temperature comprised between 10° C. and 60° C., more preferably between room temperature (25° C.) and 40° C. Preferably, the reaction mixture is left to react for a time comprised between 10 and 30 hours, more preferably between 15 and 25 hours, even more preferably of about 20 hours, in order to obtain a substantially complete conversion of the tetrahydroquinoline into the corresponding indane derivative of Formula (VII).

Advantageously, once the rearrangement reaction of step c) is complete, the acyl indane of Formula (VII) is not isolated and the reaction mixture is used as such in the next hydrolysis step d), as reported below in Scheme 8.

Scheme 8

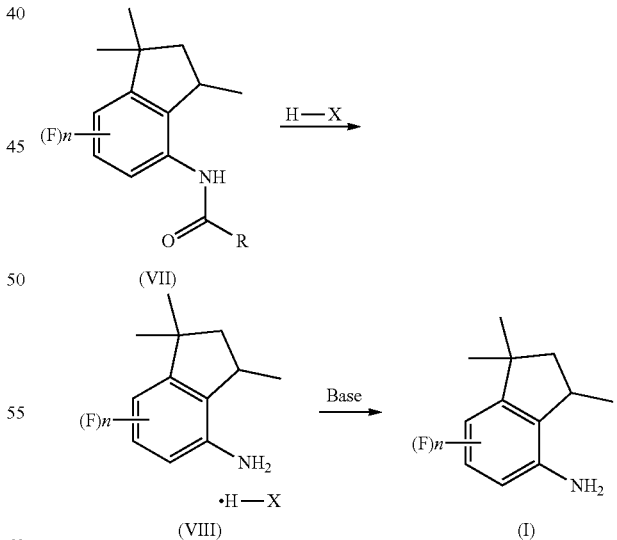

In step d), the reaction mixture of step c) containing the acyl indane of Formula (VII) is diluted with water so as to preferably obtain an acid concentration in the reaction mixture comprised between 30% and 70% by weight, more preferably between 40% and 60%, even more preferably of about 50%.

Scheme 7

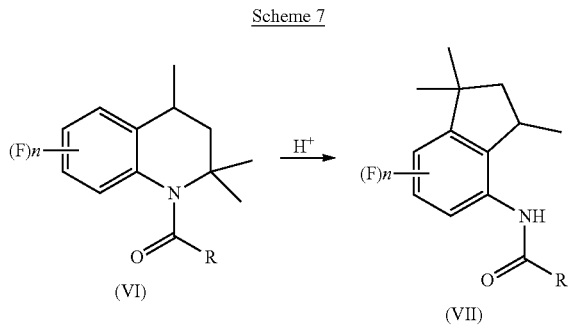

The reaction mixture is then brought to a temperature preferably comprised between 60° C. and the reflux temperature, more preferably between 95° C. and 110° C.

After a few hours at the selected temperature, the corresponding 4-aminoindane is formed, as acid addition salt of Formula (VIII).

Said salt of Formula (VIII) can be isolated and purified according to methods well known to those skilled in the art, such as precipitation or crystallization.

According to a preferred aspect of the present invention, the salt can be precipitated by adding water and the organic impurities can be removed by adding an organic solvent, preferably a solvent immiscible with water, such as an aliphatic hydrocarbon, more preferably heptane.

Subsequently, the acid addition salt of 4-aminoindane (VIII) is suspended in water and a basic solution is added so as to obtain the desired 4-aminoindane of Formula (I) in free form. The basic solution is preferably added in an amount comprised between 10% and 80% molar excess, more preferably comprised between 40% and 60% molar excess with respect to the amount of the salt of formula (VIII).

Non-limiting examples of bases suitable for the present invention are alkaline metal hydroxides, such as sodium hydroxide and potassium hydroxide, or alkaline metal carbonates.

Particularly preferred bases according to the present invention are alkaline metal hydroxides.

After the addition of the basic solution, the reaction mixture is left to react at a temperature comprised between 35° C. and 70° C., preferably between 40° C. and 60° C., more preferably of about 55° C.

As it is well known to the skilled person, different techniques can be used in order to isolate the desired product of Formula (I); for instance, the reaction mixture can be extracted by mixing it with an organic solvent slightly-miscible or immiscible with water, preferably heptane, and the organic layer can be filtered so as to remove the solid residues.

According to the present invention, the organic solution containing the 4-aminoindane of Formula (I) obtained at the end of the step (d) is preferably not concentrated and, advantageously, can be used as such for the preparation of the aminoindane amides of Formula (II).

A further object of the present invention is a process for the preparation of aminoindane amides of Formula (II),

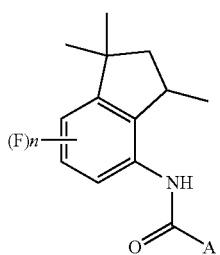

(II)

comprising the steps of:
preparing at least one 4-aminoindane derivative of Formula (I) by carrying out the steps (a)-(d) of the process described above;
condensing said 4-aminoindane derivative of Formula (I) with at least one compound of Formula

AC(O)X wherein in said formulae:
A represents a $C_6$-$C_{10}$ aryl group or a heterocyclic ring with 5 or 6 atoms containing from 1 to 3 heteroatoms selected from N, O, S, these groups being optionally substituted by one or more $R_1$ and $R_2$ groups;
$R_1$ represents a $C_1$-$C_6$ alkyl group or a $C_1$-$C_6$ haloalkyl group, said groups being optionally substituted with one or more groups selected from R', OR', $S(O)_mR'$; or $R_1$ represents a $C_3$-$C_6$ cycloalkyl group, a $C_4$-$C_9$ cycloalkylalkyl group, a $C_2$-$C_6$ alkenyl group, a $C_2$-$C_6$ alkinyl group, a $C_6$-$C_{10}$ aryl group, a $C_7$-$C_{12}$ arylalkyl group, a heterocyclic ring with 5 or 6 atoms containing from 1 to 3 heteroatoms selected from N, O, S, these groups being optionally substituted by one or more groups selected from halogen atoms, R', OR', NR'R", $S(O)_mR'$, CONR'R", COR', $CO_2R'$, CN, $NO_2$;
$R_2$ represents a $C_1$-$C_6$ alkyl group or a $C_1$-$C_6$ haloalkyl group, said groups being optionally substituted with one or more groups selected from R', OR', $S(O)_mR'$; or $R_2$ represents a $C_3$-$C_6$ cycloalkyl group, a $C_4$-$C_9$ cycloalkylalkyl group, a $C_6$-$C_{10}$ aryl group, a $C_7$-$C_{12}$ arylalkyl group, these groups being optionally substituted by one or more groups selected from halogen atoms, R', OR', $S(O)_mR'$, NR'R", CONR'R", COR', $CO_2R'$, $NO_2$, CN;
R' and R" represent a hydrogen atom, a $C_1$-$C_4$ alkyl group, a $C_1$-$C_4$ haloalkyl group;
X represents a hydroxyl group, halogen, a $C_1$-$C_6$ alkoxy group, a $C_1$-$C_6$ alkylsulfonyloxy group, a $C_6$-$C_{10}$ arylsulfonyloxy group, these groups being optionally substituted by one or more halogen atoms;
n is an integer selected within the range from 0 to 3;
m is an integer selected within the range from 0 to 2.

Examples of a $C_1$-$C_6$ alkyl group are methyl, ethyl, propyl, butyl, pentyl, hexyl.

Examples of a $C_1$-$C_6$ haloalkyl group are dichloromethyl, difluoromethyl, trichloromethyl, trifluoromethyl, chloro-difluoromethyl, dichloroethyl, trifluoroethyl, tetra-fluoroethyl, pentafluoroethyl, tetrafluoropropyl, pentafluoropropyl, dichlorobutyl, difluorobutyl, dichloropentyl, difluoropentyl, dichlorohexyl, difluorohexyl.

Examples of a $C_3$-$C_6$ cycloalkyl group are cyclopropyl, cyclobutyl, cyclopentyl, cyclohexyl.

Examples of a $C_4$-$C_9$ cycloalkylalkyl group are cyclopropylmethyl, cyclobutylmethyl, cyclopentylmethyl, cyclohexylmethyl, cyclohexylethyl, cyclohexylpropyl.

Examples of a $C_2$-$C_6$ alkenyl group are ethenyl, propenyl, butenyl, pentenyl, hexenyl.

Examples of a $C_2$-$C_6$ alkinyl group are ethinyl, propinyl, butinyl, pentinyl, hexinyl.

Examples of a $C_6$-$C_{10}$ aryl group are phenyl, naphthyl.

Examples of a $C_7$-$C_{12}$ arylalkyl group are benzyl, phenylethyl, phenylpropyl, phenylbutyl, phenylpentyl, phenylhexyl, naphthylmethyl, naphthylethyl.

Examples of a heterocyclic ring with 5 or 6 atoms containing from 1 to 3 heteroatoms selected from N, O, S, are pyrrolyl, pyrazolyl, imidazolyl, triazolyl, thiadiazolyl, oxadiazolyl, furanyl, thiophenyl, pyridyl, pyrimidyl, triazinyl.

Examples of a heterocyclic nitrogenated ring with 5 or 6 atoms are pyrrolidyl, piperidyl, morpholyl.

Examples of halogen atoms are fluorine, chlorine, bromine, iodine.

Among the aminoindane amides having general formula (II) that can be prepared with the process of the present invention, preferred are those wherein:

A represents one of the following heterocycles $A_1$-$A_5$:

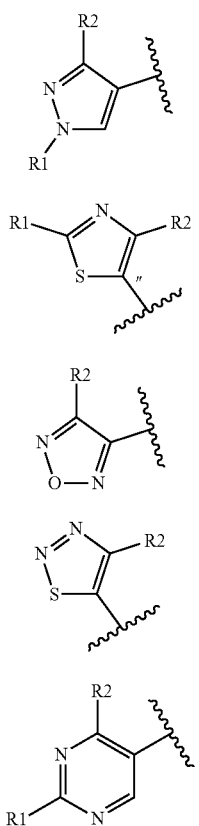

$R_1$ represents a $C_1$-$C_6$ alkyl group, a $C_1$-$C_6$ haloalkyl group or a phenyl group optionally substituted with halogen atoms, $C_1$-$C_4$ alkyl groups, $C_1$-$C_4$ haloalkyl groups, $C_1$-$C_4$ alkoxyl groups, $C_1$-$C_4$ haloalkoxyl groups;

$R_2$ represents a $C_1$-$C_6$ alkyl group, a $C_1$-$C_6$ haloalkyl group, or a phenyl group optionally substituted with halogen atoms, $C_1$-$C_4$ alkyl groups, $C_1$-$C_4$ haloalkyl groups, $C_1$-$C_4$ alkoxyl groups, $C_1$-$C_4$ haloalkoxyl groups;

Particularly preferred are the products having formula (II) wherein:

$R_1$ represents a $C_1$-$C_6$ alkyl group or a phenyl optionally substituted by halogen atoms;

$R_2$ represents a methyl, a difluoromethyl, a trifluoromethyl or a phenyl optionally substituted by halogen atoms;

Even more preferred are the products having general formula (II) wherein:

A represents $A_1$;

$R_1$ represents a methyl;

$R_2$ represents a methyl, a difluoromethyl, a trifluoromethyl.

According to a preferred aspect of the present invention, a carboxylic acid derivative of Formula AC(O)X is added to the solution of 4-aminoindane of Formula (I) obtained in step d), preferably in a molar ratio comprised between 0.9 and 1.1, more preferably between 0.95 and 1.05, even more preferably in equimolar amount with respect to the quantity of 4-aminoindane of Formula (I).

Preferably, said carboxylic acid derivative of Formula AC(O)X is an acid chloride, i.e. X represents a chlorine atom.

After the addition of the acid derivative, the reaction mixture is brought to a temperature comprised between 60° C. and the reflux temperature of the hydrocarbon solvent, preferably between 95° C. and 100° C. At the end of the condensation step, the reaction mixture can be cooled and an alkaline aqueous solution added in order to neutralize residual acidity.

The aminoindane amide of Formula (II) formed at the end of the condensation step can be subsequently isolated and possibly purified according to well-known techniques, for instance, by precipitation and subsequent filtration and washing of the solid product. The fact that the final aminoindane amide product can be isolated by filtration from the reaction mass represents a further advantage of the present invention with respect to the preparation process of the prior art.

The following examples are provided for illustrative purposes of the present invention and should be considered as being descriptive and non-limiting of the same.

EXPERIMENTAL PART

Example 1 a) Preparation of 6-fluoro-2,2,4-trimethyl-1,2-dihydroquinoline (IV)

Reaction

In a one-litre round-bottomed flask under nitrogen blanketing 4-fluoroaniline (III) (445 grams, 4.0 mol) is charged, together with $HBF_4$ (48% aqueous solution, 56 grams, 0.32 mol) and 50 mL acetone.

The flask is fitted with thermometer and a glass distillation system, comprising a vertical column filled with coarse glass rings, and condenser. An efficient magnetic stirring is employed.

The flask is heated in an external bath, set at the temperature of 150-155° C.

When the internal temperature reaches 120° C. and condensate starts being collected at the distillation end, the addition of acetone is started. Acetone is fed through PTFE tubing, ending near the bottom of the reaction mass, at the constant rate of approximately. 150-175 mL/hour, so as to maintain a very slow distillation rate. The internal temperature of the reaction is maintained in the interval 132-140° C. An overall time of 8-10 hours is employed for the supply of acetone (1500 mL), after which the reaction is stirred for further 20 min at 140° C.; the reaction mass is then cooled below 40° C.

Distillation

The distillation is performed in the same reaction vessel, maintaining the same fractioning column. The reaction mass is subjected to preliminary evaporation at 50° C. at 20-40 mbar to complete acetone and water removal.

Vacuum is applied in the range 2.0-3.0 mbar. The flask is heated, with temperature of the external bath progressively increased and reaching the final maximum of 170° C., at which the collection of the product is completed, with vacuum increased to 1.0 mbar.

Four main fractions are separated.

1. Distillate at 49-52° C. (head temperature), constituted mainly of Fluoroaniline (ca. 98%).
2. Distillate at 52-90° C., small amount of mixed fractions (4 grams).

3. Distillate at 92-102° C. constituting the product dihydroquinoline.
4. Residue in the flask: dark dense material (tars), that solidifies on cooling.

The results of the representative experiment, including the recovery of Fluoroaniline, in term of weight and molar yields were:

Dihydroquinoline (as ca. 95% GCA purity distilled material): 340 grams, ca. 42%
Dihydroquinoline yield (overall available): ca. 43%
Recovered 4-Fluoroaniline yield (overall available): ca. 42%
Dihydroquinoline yield, calculated on consumed 4-Fluoroaniline: ca. 72%

Distilled 4-Fluoroaniline and any mixed fractions are sent to recycle in a successive batch.

b) Preparation of 6-fluoro-2,2,4-trimethyl-1,2,3,4-tetrahydroquinoline (V)

The crude liquid Dihydroquinoline (IV) (96% purity, 106 grams, 0.530 mol) is dissolved in 400 mL heptane and extracted with 200 mL 1% aqueous hydrochloric acid. The aqueous layer is discarded and the organic solution is transferred to a 1-litre hydrogenation autoclave. Catalytic palladium on carbon (10%, 2.5 grams) is charged, hydrogen gas is introduced at 3 bar pressure and reaction performed at 30° C. for 2 hours.

After filtration of the catalyst, the solvent is completely removed by distillation, thus obtaining 100.0 grams crude Tetrahydroquinoline (V), having purity 98.5%.

c) Preparation of 1-acetyl-6-fluoro-2,2,4-trimethyl-1,2,3,4-tetrahydroquinoline (VI)

In a one-litre round-bottomed flask with mechanical stirring under nitrogen blanketing, Tetrahydroquinoline (V) (98% purity, 100.0 grams, 0.506 mol) is mixed with acetic anhydride (60.0 grams, 0.58 mol).

The reaction mixture is heated in an external bath, set at the temperature of 150° C., with internal temperature reaching 134 to 138° C. at which it is maintained for 5 hours. Further excess acetic anhydride (1.0 g) can be added to achieve complete conversion.

The reaction mixture is refrigerated to ca. 40° C., and water (2.0 mL) is added to decompose excess acetic anhydride.

The liquid (acetic acid) is distilled from the reaction vessel at reduced pressure (60 mbar and then 20 mbar; with temperature in the range 70-90° C.).

The semi-solid residue is consequently taken up with heptane (300 mL) and again subjected to complete distillation at atmospheric pressure, with internal temperature 98-124° C., in order to completely remove acetic acid.

More heptane (150 mL) is added, so as to obtain a complete solution at 95° C. The mass is then allowed to cool slowly to 20° C. with stirring, in order to cause the precipitation of a finely divided solid product.

d) Preparation of 7-fluoro-1,1,3-trimethylindan-4-ylamine sulfate (VIII)

In a one-litre round-bottomed flask with mechanical stirring sulfuric acid (93% concentration, 375 grams, 3.50 mol) is initially charged.

The acetyl-tetrahydroquinoline (VI) (119 grams, 0.50 mol) heptane suspension from step c is slowly added into the sulfuric acid layer with efficient stirring while the mass temperature is controlled between 15 and 20° C. The resulting biphasic suspension is then maintained with stirring at 34-36° C. for 20 hours.

One additional hour with temperature increased to 48-50° C. is allowed for completing the conversion.

To the reaction mass water (320 mL) is slowly added under stirring with strong exotherm (in order to obtain ca. 50% $H_2SO_4$ concentration). The reaction mass is progressively heated and heptane is distilled off, with collection of organic layer (170 mL) and some water.

The solution is then heated to a reflux (110-111° C., internal temperature) and maintained 5 hours.

The reaction mass is refrigerated to 40° C. and slowly poured into ice-cold water (1000 grams) with evident exotherm (in order to obtain ca. 20% $H_2SO_4$ concentration) in a 2-litre vessel with mechanical stirring. The final temperature is adjusted around 20° C. and the resulting slurry of indanamine sulfate salt (VIII) is filtered. The solid is washed on the filter with 150 mL water, followed by heptane (250 mL).

The filtration cake is sucked on the filter for sufficient time, then the wet solid (approximately 180 grams) is sent to salt un-blocking.

e) Preparation of 7-fluoro-1,1,3-trimethylindan-4-ylamine (I)

The solid indanamine sulfate salt (total amount, 0.450 mol) is added to 400 grams aqueous solution containing NaOH (28 grams, 0.68 mol) in a 2-litre flask. To the alkaline suspension heptane (400 mL) is added and the whole is stirred with heating to 55° C. After complete solids dissolution, the phases are separated. The aqueous layer is extracted again with heptane (300 mL) at 55° C. The combined warm heptane solution (540 grams) is filtered on a layer of celite to remove some undissolved material.

Part of the heptane is distilled off at reduced pressure (275 mbar, 57° C.), in order to azeotropically remove some traces of water and reach the suitable volume for use in next Step. The final weight of the solution is approximately 460 grams, containing around 89.0 grams indanamine (I)

Example 2 a) Preparation of 1-methyl-3-(difluoromethyl)-1H-pyrazole-4-carbonyl chloride (A=A$_1$ in which R$_1$=methyl, R$_2$=difluoromethyl)

The pyrazole acid chloride is prepared from 3-difluoromethyl-1-methyl-1H-pyrazole-4-carboxylic acid and thionyl chloride in heptane shortly before use.

In a 500-mL round-bottomed flask provided with alkaline scrubber, pyrazole acid (74.0 grams, 0.42 mol) is suspended in heptane (170 mL). Dimethylformamide (0.70 grams, 0.009 mol) and thionyl chloride (55.0 grams, 0.462 mol) are added and the bi-phasic mixture is stirred and heated at 42-45° C.

After complete conversion of pyrazole acid (2.5 hours), the solvent and excess thionyl chloride are completely removed by vacuum distillation.

Liquid pyrazole acid chloride is obtained as the residue (approximately 81.0 grams).

b) Preparation of 3-difluoromethyl-N-(7-fluoro-1,1,3-trimethyl-4-indanyl)-1-methyl-4-pyrazolecarboxamide (II), A=A₁ in which R₁=methyl, R₂=difluoromethyl A 2-litre glass reactor with efficient mechanical stirrer, reflux condenser and alkaline scrubber is employed.

To the indanamine heptane solution (I) (total amount, 460 grams, 0.46 mol indanamine) at 50° C., the liquid pyrazole acid chloride obtained in step a) is added during ca. 10 min at 50-70° C. with exothermic reaction and formation of a precipitate. More heptane (20 mL) is used for rinsing.

The reaction is stirred at reflux (95-97° C. internal temperature) during 4 hours, after which the reaction is completed. The evolution of HCl ceases within 3 hours.

The resulting reaction suspension is refrigerated below 30° C., then NaOH aqueous solution (215 mL, 2.5% concentration) is added, and the mixture stirred at least 30 min, while the temperature is adjusted to 22° C.

The slurry is filtered on a flat sintered glass filter and the solid washed at 45° C. with water (250 mL) after re-slurrying and stirring.

The resulting solid is filtered again and washed on the filter with water, (250 mL, or until resulting pH is neutral) and successively with heptane (250 mL).

After aspiration on the filter for 1 hour, the moist solid (165 grams) is dried in a vacuum oven at 55° C.

The desired product is obtained (approximately 140 grams, with assay 98%).

Heptane mother liquors contain excess indanamine, which is sent to recycle.

Example 3 (Comparative)

a) Preparation of 6-fluoro-2,2,4-trimethyl-1,2-dihydroquinoline

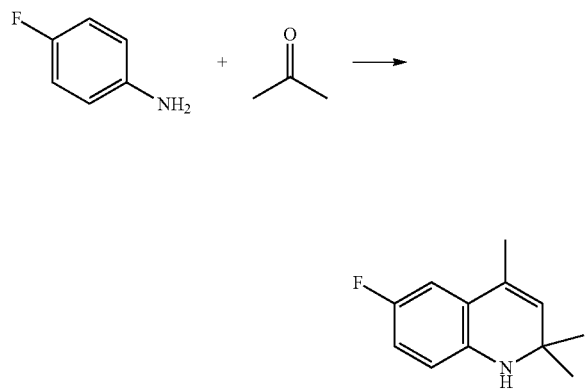

Step 1 is run according to Example 1, step a). In addition, the resulting distilled dihydroquinoline is dissolved in a proper solvent and stirred with 1% aqueous solution of hydrochloric acid, in order to remove any residual 4-fluoroaniline and reach around 98% purity. Said solvent is removed by vacuum distillation before running the following step.

b) Preparation of 1-acetyl-6-fluoro-2,2,4-trimethyl-1,2-dihydroquinoline

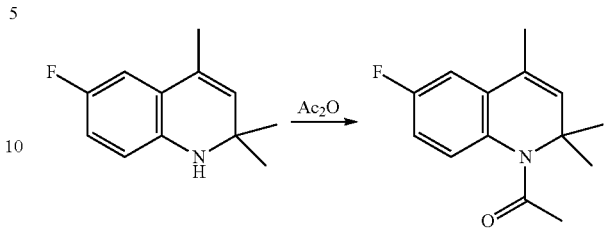

In a one-litre round-bottomed flask with mechanical stirring under nitrogen blanketing, Dihydroquinoline (98% purity, 104.0 grams, 0.533 mol) is mixed with acetic anhydride (65.0 grams, 0.635 mol).

The reaction mixture is heated in an external bath, set at the temperature of 150° C., with internal temperature reaching around 138° C. at which it is maintained for 5 hours to achieve complete conversion.

The reaction mixture is refrigerated to ca. 40° C., and water (3.0 mL) is added to decompose excess acetic anhydride.

The liquid (acetic acid) is distilled from the reaction vessel at reduced pressure (60 mbar and then 20 mbar; with temperature in the range 70-90° C.).

The oily residue is consequently taken up with heptane (300 mL) and again subjected to complete distillation at atmospheric pressure, with internal temperature 96-125° C., in order to completely remove acetic acid.

More heptane (500 mL) is added, so as to obtain a complete solution at 65° C. The mass is kept at temperature around 50° C. and transferred to the following stage.

c) Preparation of 1-acetyl-6-fluoro-2,2,4-trimethyl-1,2,3,4-tetrahydroquinoline

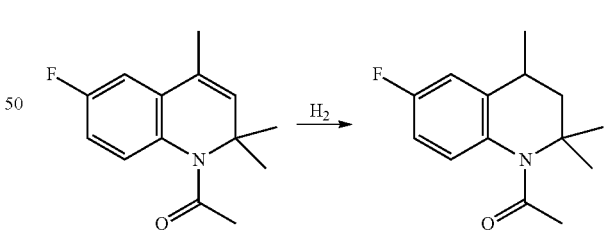

The organic solution is transferred to a 1-litre hydrogenation autoclave under nitrogen. Catalytic palladium on carbon (10%, 2.5 grams) is charged, hydrogen gas is introduced at 3 bar pressure and reaction performed at 50° C. for 2 hours.

After filtration of the catalyst, the solvent is partly removed by vacuum distillation, and eventually refrigerated to 20° C., thus obtaining 119 grams crude acetyl-THQ, having purity 98%, as the approximately 240 grams heptane suspension.

d) Preparation of
7-fluoro-1,1,3-trimethylindan-4-ylamine

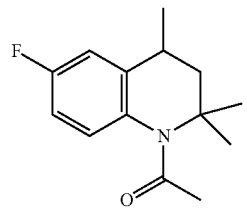

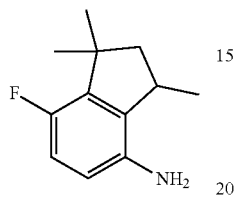

In a one-litre round-bottomed flask with mechanical stirring sulfuric acid (93% concentration, 375 grams, 3.50 mol) is initially charged.

The acetyl-THQ (119 grams, 0.50 mol) heptane suspension from Step 3 is slowly added into the sulfuric acid layer with efficient stirring while the mass temperature is controlled between 15 and 20° C. The resulting biphasic suspension is then maintained with stirring at 34-36° C. during 20 hours.

One additional hour with temperature increased to 48-50° C. is allowed for completing the conversion.

To the reaction mass water (320 mL) is slowly added under stirring with strong exotherm (in order to obtain ca. 50% $H_2SO_4$ concentration). The reaction mass is progressively heated and heptane is distilled off, with collection of organic layer (170 mL) and some water.

The solution is then heated to a reflux (110-111° C., internal temperature) and maintained 5 hours.

The reaction mass is refrigerated to 40° C. and slowly poured into ice-cold water (1000 grams) with evident exotherm in a 2-litre vessel with mechanical stirring. The final temperature is adjusted around 20° C. and the resulting slurry of indanamine sulfate salt is filtered. The solid is washed on the filter with 150 mL water, followed by heptane (250 mL).

The wet filtration cake is then added to 400 grams aqueous solution containing NaOH (28 grams, 0.68 mol) in a 2-litre flask. To the alkaline suspension heptane (400 mL) is added and the whole is stirred with heating to 55° C. After complete solids dissolution, the phases are separated. The aqueous layer is extracted again with heptane (300 mL) at 55° C. The combined warm heptane solution (540 grams) is filtered on a layer of celite to remove some undissolved material.

When heptane is completely distilled off at reduced pressure, a dark solid residue is obtained, constituted of approximately 89.0 grams indanamine free-base, having purity above 99%.

The invention claimed is:

1. A process for preparation of 4-aminoindane compounds of Formula (I), salts and enantiomers thereof

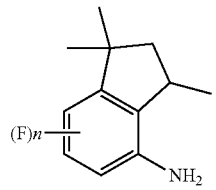

comprising the steps of:

a) hydrogenating a 1,2-dihydroquinoline of Formula (IV)

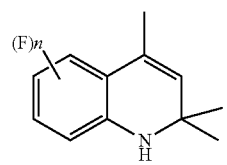

to give a corresponding tetrahydroquinoline of Formula (V)

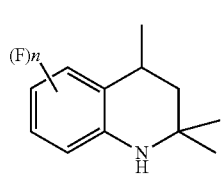

b) acylating the tetrahydroquinoline of Formula (V) with a carboxylic acid derivative of Formula RC(O)LG to obtain a corresponding acyl derivative compound of Formula (VI) in a reaction mixture

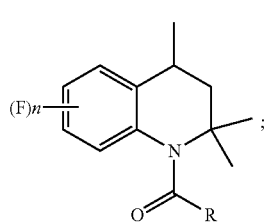

c) rearranging the acyl derivative compound of Formula (VI) under acidic conditions so as to give an acyl indane compound of Formula (VII) or an addition salt thereof to give a corresponding tetrahydroquinoline of Formula (V)

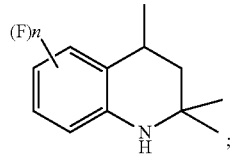

(V)

b) acylating the tetrahydroquinoline of Formula (V) with a carboxylic acid derivative of Formula RC(O)LG to obtain a corresponding acyl derivative compound of Formula (VI)

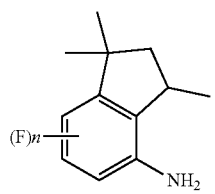

(VI)

c) rearranging the acyl derivative compound of Formula (VI) under acidic conditions so as to give an acyl indane compound of Formula (VII) or an addition salt thereof

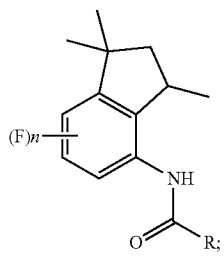

(VII)

and
d) hydrolyzing the acyl group of the acyl indane compound of Formula (VII) so as to obtain the 4-aminoindane compounds of Formula (I), salts and enantiomers thereof;
wherein in the formulae:
n is an integer selected within the range from 0 to 3, inclusive;
R is a $C_1$-$C_6$ alkyl group or a $C_6$-$C_{10}$ aryl group, these groups being optionally substituted with one or more of: $C_1$-$C_6$ alkyl groups or halogen atoms; and
LG is a leaving group selected from: (i) a hydroxy group; (ii) a halogen atom; (iii) a $C_1$-$C_6$ alkylsulfonyloxy group; (iv) a $C_6$-$C_{10}$ arylsulfonyloxy group; or (v) a $R_a$ aCOO group wherein $R_a$ is a $C_1$-$C_6$ alkyl group, the groups (iii)-(v) being optionally substituted with one or more halogen atoms; and
the process further comprising:
adding an organic solvent to the reaction mixture obtained at the completion of step (b); and
prior to step (c), distilling the organic solvent from the reaction mixture to remove any excess of the carboxylic acid derivative of Formula RC(O)LG and to form a slurry comprising the acyl derivative compound of Formula (VI).

2. The process of claim 1, wherein the slurry comprising the acyl derivative compound of Formula (VI) is fed to step (c).

3. A process for preparation of 4-aminoindane compounds of Formula (I), salts and enantiomers thereof

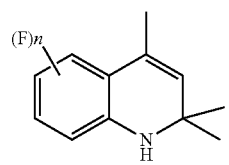

(I)

comprising the steps of:
a) hydrogenating a 1,2-dihydroquinoline of Formula (IV)

(IV)

to give a corresponding tetrahydroquinoline of Formula (V)

b) acylating the tetrahydroquinoline of Formula (V) with a carboxylic acid derivative of Formula RC(O)LG to obtain a corresponding acyl derivative compound of Formula (VI)

c) rearranging the acyl derivative compound of Formula (VI) under acidic conditions so as to give an acyl indane compound of Formula (VII) or an addition salt thereof and
d) hydrolyzing the acyl group of the acyl indane compound of Formula (VII) so as to obtain the 4-aminoindane compounds of Formula (I), salts and enantiomers thereof;
wherein in the formulae:
n is an integer selected within the range from 0 to 3, inclusive;
R is a $C_1$-$C_6$ alkyl group or a $C_6$-$C_{10}$ aryl group, these groups being optionally substituted with one or more of: $C_1$-$C_6$ alkyl groups or halogen atoms; and
LG is a leaving group selected from: (i) a hydroxy group; (ii) a halogen atom; (iii) a $C_1$-$C_6$ alkylsulfonyloxy group; (iv) a $C_6$-$C_{10}$ arylsulfonyloxy group; or (v) a $R_a$ aCOO group wherein $R_a$ is a $C_1$-$C_6$ alkyl group, the groups (iii)-(v) being optionally substituted with one or more halogen atoms; and
wherein step (c) comprises suspending the acyl derivative compound of Formula (VI) in an organic solvent and contacting the thus obtained suspension with an organic acid or an inorganic acid so as to obtain the acyl indane compound of Formula (VII) in a form of an addition salt.

4. The process of claim 3, further comprising:

forming a slurry comprising the acyl indane compound of Formula (VII) in the form of the addition salt;

wherein the slurry comprising the acyl indane compound of Formula (VII) in the form of the addition salt is fed to step (d).

5. The process of claim 3, wherein the acyl indane compound of Formula (VII) in the form of the addition salt is contacted with an alkaline aqueous solution so as to obtain the 4-aminoindane compounds of Formula (I), salts and enantiomers thereof.

6. A process for preparation of 4-aminoindane compounds of Formula (I), salts and enantiomers thereof

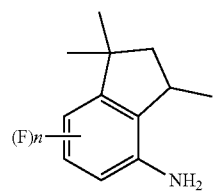

(I)

comprising the steps of:

a) hydrogenating a 1,2-dihydroquinoline of Formula (IV)

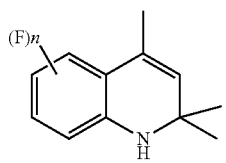

(IV)

to give a corresponding tetrahydroquinoline of Formula (V)

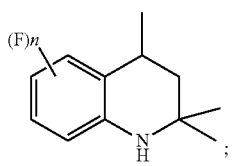

(V)

b) acylating the tetrahydroquinoline of Formula (V) with a carboxylic acid derivative of Formula RC(O)LG to obtain a corresponding acyl derivative compound of Formula (VI)

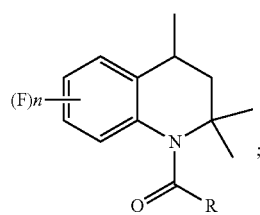

(VI)

c) rearranging the acyl derivative compound of Formula (VI) under acidic conditions so as to give an acyl indane compound of Formula (VII) or an addition salt thereof

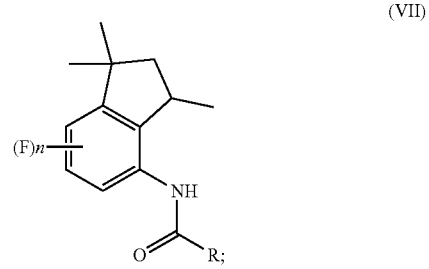

(VII)

and d) hydrolyzing the acyl group of the acyl indane compound of Formula (VII) so as to obtain the 4-aminoindane compounds of Formula (I), salts and enantiomers thereof;

wherein in the formulae:

n is an integer selected within the range from 0 to 3, inclusive;

R is a $C_1$-$C_6$ alkyl group or a $C_6$-$C_{10}$ aryl group, these groups being optionally substituted with one or more of: $C_1$-$C_6$ alkyl groups or halogen atoms; and LG is a leaving group selected from: (i) a hydroxy group; (ii) a halogen atom; (iii) a $C_1$-$C_6$ alkylsulfonyloxy group; (iv) a $C_6$-$C_{10}$ arylsulfonyloxy group; or (v) a $R_a$COO group wherein $R_a$ is a $C_1$-$C_6$ alkyl group, the groups (iii)-(v) being optionally substituted with one or more halogen atoms; and wherein step (c) comprises suspending the acyl derivative compound of Formula (VI) in an organic solvent and contacting the thus obtained suspension with sulfuric acid or orthophosphoric acid so as to obtain the acyl indane compound of Formula (VII) in a form of an addition salt.

7. The process of claim 1, wherein the organic solvent is selected from: aliphatic or cycloaliphatic hydrocarbons, chlorinated hydrocarbons, aromatic hydrocarbons, alcohols, glycols, esters, or mixtures thereof.

8. The process of claim 1, wherein the organic solvent is selected from: hexane, heptane, methylene chloride, dichloroethane, methanol, ethanol, isopropanol, toluene, ethyl acetate, or mixtures thereof.

9. The process of claim 3, wherein the organic solvent is selected from: aliphatic or cycloaliphatic hydrocarbons, chlorinated hydrocarbons, aromatic hydrocarbons, alcohols, glycols, esters, or mixtures thereof.

10. The process of claim 3, wherein the organic solvent is selected from: hexane, heptane, methylene chloride, dichloroethane, methanol, ethanol, isopropanol, toluene, ethyl acetate, or mixtures thereof.

11. The process of claim 1, wherein step (a) comprises:

dissolving the 1,2-dihydroquinoline of Formula (IV) in an organic solvent; and contacting the 1,2-dihydroquinoline of Formula (IV) dissolved in the organic solvent with gaseous hydrogen in the presence of a hydrogenation catalyst so as to obtain the tetrahydroquinoline of Formula (V).

12. The process of claim 1, wherein step (a) comprises:

dissolving the 1,2-dihydroquinoline of Formula (IV) in a polar solvent; and contacting the 1,2-dihydroquinoline of Formula (IV) dissolved in the polar solvent with gaseous hydrogen in the presence of a hydrogenation catalyst so as to obtain the tetrahydroquinoline of Formula (V).

13. The process of claim 1, wherein step (b) is carried out in the absence of added solvent.

14. The process of claim 3, wherein step (a) comprises:
dissolving the 1,2-dihydroquinoline of Formula (IV) in an organic solvent; and
contacting the 1,2-dihydroquinoline of Formula (IV) dissolved in the organic solvent with gaseous hydrogen in the presence of a hydrogenation catalyst so as to obtain the tetrahydroquinoline of Formula (V).

15. The process of claim 3, wherein step (a) comprises:
dissolving the 1,2-dihydroquinoline of Formula (IV) in a polar solvent; and
contacting the 1,2-dihydroquinoline of Formula (IV) dissolved in the polar solvent with gaseous hydrogen in the presence of a hydrogenation catalyst so as to obtain the tetrahydroquinoline of Formula (V).

16. The process of claim 3, wherein step (b) is carried out in the absence of added solvent.

17. The process of claim 3, wherein the inorganic acid is sulfuric acid.

18. The process of claim 6, wherein step (a) comprises:
dissolving the 1,2-dihydroquinoline of Formula (IV) in an organic solvent; and
contacting the 1,2-dihydroquinoline of Formula (IV) dissolved in the organic solvent with gaseous hydrogen in the presence of a hydrogenation catalyst so as to obtain the tetrahydroquinoline of Formula (V).

19. The process of claim 6, wherein step (a) comprises:
dissolving the 1,2-dihydroquinoline of Formula (IV) in a polar solvent; and
contacting the 1,2-dihydroquinoline of Formula (IV) dissolved in the polar solvent with gaseous hydrogen in the presence of a hydrogenation catalyst so as to obtain the tetrahydroquinoline of Formula (V).

20. The process of claim 6, wherein step (b) is carried out in the absence of added solvent.

* * * * *